United States Patent [19]

Okker et al.

[11] Patent Number: 5,019,501

[45] Date of Patent: May 28, 1991

[54] PROCESS FOR THE ACTIVATION OF PROMOTERS OF BACTERIA

[75] Inventors: Robert J. H. Okker, Oegstgeest; Egbertus J. J. Lugtenberg, Woerden; Robbert A. Schilperoort, Anthonie Duycklaan 10c, 2334 CD Leiden, all of Netherlands

[73] Assignees: Rijksuniversileit Leiden; Robbert Adriaan Schilperoort, both of Leiden, Netherlands

[21] Appl. No.: 317,062

[22] Filed: Feb. 28, 1989

Related U.S. Application Data

[63] Continuation of Ser. No. 737,153, May 23, 1985, abandoned.

[30] Foreign Application Priority Data

Jun. 4, 1984 [NL] Netherlands .................. 8401781

[51] Int. Cl.$^5$ ............... C12P 21/00; C12N 15/00; C12N 15/03; C12N 15/05; C12N 15/70; C12N 15/67; A01C 1/00
[52] U.S. Cl. ................... 435/69.1; 435/172.3; 435/320.1; 435/252.3; 435/252.33; 47/58; 935/25; 935/29; 935/67
[58] Field of Search ............... 435/68, 70, 71, 91, 435/172.1, 172.3, 320, 243, 252.3, 252.31-252.35, 69.1, 71.1, 71.2, 71.3; 536/27; 800/1; 47/58; 935/6, 25, 29, 35, 67, 72-75

[56] References Cited

U.S. PATENT DOCUMENTS 4,658,082  4/1987  Simpson et al. .................. 800/1

FOREIGN PATENT DOCUMENTS 0167192  8/1986  European Pat. Off. ......... 435/172.3

OTHER PUBLICATIONS

Melchers et al, "Virulence of Agrobacterium", Oxford Surveys of Plant Molecular and Cell Biology, vol. 4 (1987), pp. 167-220.
Lundquist et al, Chem. Abstr. 106:44792w (1985).
Okker et al, Chem. Abstr. 106:44698v (1985).
Okker et al., Nature 312: 564 (1984).
Hille et al, J. Bacteriol. 158: 754 (1984).
Hoekema et al, Nature 303: 179 (1983).

*Primary Examiner*—James Martinell
*Attorney, Agent, or Firm*—Ladas & Parry

[57] ABSTRACT

A process for the activation of genes in micro-organisms, in which genes not occurring as such in nature are activated by contact with plants or with the substance or substances causing the activation and present or not in plant fragments or plant exudates, the genes used consisting of one or more proteins encoding fragments of one or more natural genes and/or one or more synthetically produced DNA-sequences, which encode for one or more proteins and a promotor region originating from one of the genes naturally present in micro-organisms and being of such a nature that respectively the effecting or omitting of the above-mentioned contact makes it possible to activate the artificially constructed gene or genes or to stop the activity of the gene or genes, respectively.

17 Claims, 1 Drawing Sheet

PROCESS FOR THE ACTIVATION OF PROMOTERS OF BACTERIA

This is a continuation of co-pending application Ser. No. 06/737,153 filed on May 23, 1985 (now abandoned).

BACKGROUND OF THE INVENTION

The genes of the Vir-region of the Ti-plasmid of *A. tumefaciens*, which are essential for the virulence properties of the bacterium, are not expressed or are only minimally expressed when the bacteria are cultivated on standard synthetic media. This is based on the fact that the relevant promotor regions of the genes are not sufficiently activated.

SUMMARY OF THE INVENTION

It has now been found that, for good activation, the bacteria should be in contact with a wounded or non-wounded plant or substances originating from plants. The induction of a promotor of virC described herein not only occurs in *A. tumefaciens*, but also if the promotor is recombined in *E. coli*, a bacterium that is not closely related to *A. tumefaciens*. These or similar promotors also occur on other Ti-plasmids, on Ri-plasmids (from A. rhizogenes), on the sym-plasmid of Rhizobium and possibly also in other plant-related micro-organisms. Now, this discovery makes it possible by placing such promotors before certain genes to have these genes express conditionally. This invention is applicable to a wide range of micro-organisms. The promotor could, for instance, be applied to the construction of Pseudomonas strains which, when in contact with plants, proceed to the production of siderophores (siderophores are substances which by protection against plant pathogens have a yield increasing effect). In this connection one may also think of other proteins which are produced by suitable micro-organisms for protection, growth promotion and product increase of a crop which may be contacted with the micro-organisms in question in no matter which way. Thus, protection can be directed to effecting resistance against agricultural chemicals, insects, pathogens, cold, dryness and salination ("salt" resistance). These promotors also open possibilities for starting, at any desirable time, production in batch cultures of substances that are detrimental to or otherwise growth-inhibiting for the production of micro-organisms or cells.

DETAILED DESCRIPTION OF THE DRAWING

Figure 1:
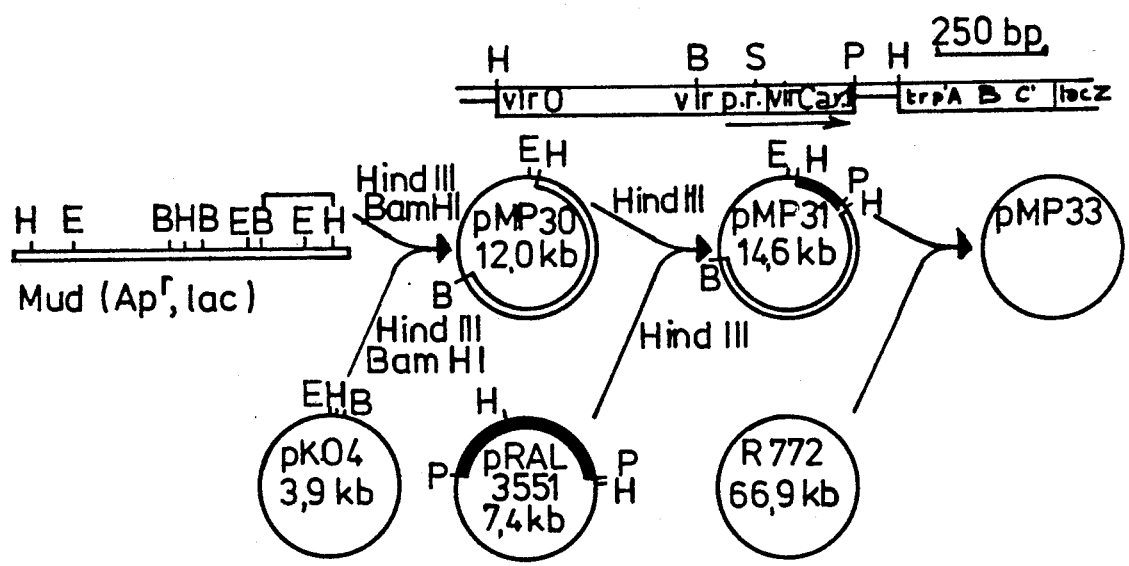

FIG. 1—construction of the lacZ—virC promoter constructs via use of plasmids pMP 30, pMP 31 and pMP 33.

*Agrobacterium tumefaciens* is capable of providing cells of most of the angiospermous plants with new genetic properties. This transformation results in tumor formation in dicotyledonous plants. Tumour formation does not occur in any of the monocotyledonous plants, but, as was found recently, some monocotyledonous types can be transformed by *A.tumefaciens* (Dutch patent application 84 01048). The genes responsible for this transformation are situated on the tumour-inducing (Ti) plasmid present in virulent strains (Van Larebeke et al., Nature (London) 252, 169-170 (1974); Zaenen et al., J.Mol. Biol. 86, 109-127 (1974)). Two regions on the Ti-plasmid are essential for tumour induction. The T-region is the part of the Ti-plasmid that is transferred to the plant cell, is integrated in the nuclear DNA there, and contains genes which are responsible for the tumour nature of the transformed plant cell (Chilton et al., Cell 11, 263-271 (1977); Ooms et al., Gene 14, 33-50 (1981)).

In addition to the T-region there is a second region on the Ti-plasmid essential for the virulence properties of the bacterium (Ooms et al., J. Bacteriol., 144, 82-91 (1980); Garfinkel et al., J. Bacteriol. 144, 732-743 (1980)). Mutations in this Vir (virulence) region cause avirulence or host-specific weakened virulence. In the Vir-region there are seven loci (vir A, B, C, D, E,F and 0). Mutants in these loci are all complementary in trans by the genes present in nature, present on clones or R'-plasmids (Hille et al., Plasmid 7, 107-118 (1982); Klee et al., J. Bacteriol. 150, 327-331 (1982)). This is an indication that the products of these genes perform their function within the bacterium.

The results obtained show that the virulence genes of the Ti plasmid do not express when the bacteria are cultivated on standard media, but that both in *A. tumefaciens* and in *E-coli*, bacteria not at all related to one another, can be stimulated by substances which are exuded by plants. Exudation of these substances also occurs in the absence of the micro-organisms.

In order to be able to detect the activity of the virulence genes lacZ plasmids were used. The promotor region of virC (a promotor is situated before the part of a gene which is translated into a peptide chain and contains all signals necessary for the expression of a gene) was cloned for the lacZ gene of *E. coli* which no longer had a promotor structure. Plasmid pMP30 (see FIG. 1) contains the complete lacZ gene without promotor. LacZ encodes for the enzyme $\beta$-galactosidase. The activity of this enzyme can simply be detected on indicator media with the chromophore 5-bromo-4-chloro-3-indolyl-$\beta$-D-galactopyranoside (shorted X-gal.). Degradation of X-gal by the enzyme gives a blue colored disintegration product.

Since the lacZ-gene in pMP 30 does not contain a promotor, an *E-coli Lac* with this plasmid does not show $\beta$-galactosidase activity. In the unique HindIII site of pMP30 a 2.6 kbp HindIII fragment was cloned containing the promotor region and a part of the structural gene of virC. The orientation of the 2.6 kbp fragment in the resulting plasmid pMP31 is such that the promotor of virC is directed towards lacZ (FIG. 1). Bacterial strains containing pMP30 and pMP31 as described above, have been deposited with Centraalbureau voor Schimmelcultures (CBS), Oosterstraat 1, Postbus 273, NL-3740 AG, BAARN, Netherlands under Accession Nos. 718.87 and 719.87 respectively.

An *E. coli* del.lac strain with the plasmid pMP31 shows on agar plates with X-gal a weak but significant blue coloration after a 60-hour incubation. An *E.coli* del.lac strain is a strain in which the *E. coli*'s own lac-gene is deleted. In liquid media no $\beta$-galactosidase activity was detected. The plasmids pMP 30 and pMP 31 cannot be maintained in *A tumefaciens*. In order to be able to test the plasmids for their activity in *A. tumefaciens*, cointegrates were constructed with the plasmid R772, a conjugative plasmid having a wide host range. The cointegrates of pMP30 and pMP31 with R772 were called respectively pMP32 and pMP33. Agrobacterium strains with pMP32 or pMP33 do not show $\beta$-galactosidase activity, not even when, in addition to these plasmids, the Ti-plasmid is present. So, under standard conditions, virC does not express in *A. tumefaciens* or *E. coli* or only barely.

The possibility that the virulence genes express only under the influence of plant substances was tested by growing E. coli (pMP31) and A. tumefaciens (pMP33) in the presence of exudates of dicotyledonous and monocotyledonous plant types. For the preparation of exudates newly germinated seeds or root tissue, after washing with synthetic growing media for E. coli or A. tumefaciens, were incubated for 4-5 hours in the very same media (1 to 3 seeds per ml or medium; 0.1 g of root tissue per ml of medium). After filtration, in order to get rid of plant fragments, the exudates were inoculated with bacteria ($5 \times 10^7$ bacteria per ml) and incubated for 16 hours at 29° C. in the presence of 120 $\mu$g.ml$^{-1}$ X-gal. The blue color is a measure for the $\beta$-galactosidase activity under the direction of the virC-promotor. As is shown in table 1, exudates of dicotyledonous as well as of some monocotyledonous plants appeared capable of a strong induction of the virC-promotor, resulting in considerable $\beta$-galactosidase activities. Surprisingly, this inducing effect was also found in E. coli strains.

Exudates of monocotyledonous plants gave results dependent on the plant type used. Allium cepa (onion) exudate gave induction of the virC-promotor comparable with the induction by exudates of dicotyledonous plants, whereas exudates of Zea mays (maize) hardly showed any induction. It also appeared that the inducing substance was also exuded by plant cells already transformed. Control experiments with E. coli (pMP30) and A. tumefaciens (pMP32) gave no or only weak $\oplus$-galactosidase activities in the presence of plant exudates. The very weak activity of A. tumefaciens (pMP32) also occurred when no plasmids with lacZ were present and so is the result of endogeneous $\beta$-galactosidase activity of A. tumefaciens.

It was concluded from these results that the promotor of virC is not active under standard conditions, but that same is strongly activated by a substance (substances) which is (are) exuded by dicotyledonous and monocotyledonous plants. This is the first time that a bacterium promotor is described, which is activated under the influence of substances normally occurring in the plant. That this substance or these substances is/are also separated by tumour tissue is in accordance with recent results, which point out that tumor tissue is also transformable by A. tumefaciens (Van Slogteren et al., Nature, submitted (1984).

The characterization of the inducing agent of the virC promotor as it is present in the exudate of the pea has been started. In the presence of a number of low-molecular substances, which can be expected in exudate no induction of the virC promotor was found in E. coli (table 2). The inducing substance (or substances) turned out to be heat labile. After a 15-minute incubation at 55° C. of the exudates the inducing effect on the virC-promotor had completely vanished. Treatment of the exudates with RNase, DNase, phospholipase A2 and phospholipase D had no effect upon the inducing activity of the exudate. Treatment of the exudate with the protein splitting enzymes pronase and trypsine (20 $\mu$g.ml$^{-1}$), however, resulted in the inducing activity completely vanishing. The treatment with these enzymes had no influence on the capacity of induction of the lac-genes in the strain E. coli Flac$^+$:del (lac-pro) (table 3).

Dialysis of the pea exudate by membranes having a pore size which let molecules having a mass of less than 7kD pass did not show loss of inducing activity.

It was shown that the virulence genes of the Ti-plasmid of A. tumefaciens do not express when the bacteria are grown in standard media, but that they are induced when they are contacted with the plant or with plant substances. This discovery is essential scientifically, because it offers openings to further clarify the function of the virulence genes in the process of tumour induction and transformation. Besides this discovery offers possibilities to use the promotors of such genes for biotechnological applications. The fact that induction of the virC-promotor does not only occur in Agrobacterium but also in a bacterium that is very remote from Agrobacterium, like E.-coli, makes this type of promotor suitable for use in a wide scale of bacterial or microorganisms in general which show interaction with plants. Bacterial processes which are useful for the plant, but are detrimental to the bacterium itself, can specifically be switched on in the position where said promotors are to perform their function.

TABLE 1

Induction of the virC-promotor under the influence of plant exudates.

| | E. coli | | A. tumefaciens | | |
|---|---|---|---|---|---|
| | pMP31 (+VirC) | pMP30 (−virC) | pMP33 (+virC) | pMP32 (−virC) | no bacteria |
| Exudates | | | | | |
| Pisum sativum | ++ | − | + | ± | − |
| Vicia hirsuta | ++ | − | nd | nd | − |
| Daucus carota [1] | ++ | − | + | ± | − |
| Nicotiana plum.[1] baginifolia | ++ | − | nd | nd | − |
| Allium cepa | ++ | − | + | ± | − |
| Zea mays | − | − | +/± | ± | − |
| Minimum medium | − | − | | ± | ± | − |

[1]Root cultures of tissues infected with A. rhizogenes

TABLE 2

Influence of a number of low-molecular substances on the induction of the virC-promotor

| Tested substances | | | Induction virC in E. coli del. lac. (pMP31) |
|---|---|---|---|
| amino acids | 0.3% | casimonacids | − |
| vitamins | 400 ng · ml$^{-1}$ | pantothenic acid | − |
| | | nicotinic acid | − |
| | | p-amino-benzoic acid | − |
| | | pyridoxin | − |
| | | thiamine | − |
| sugars | 6.6 mg · ml$^{-1}$ | arabinose | − |
| | | lactose | |
| | | galactose, sorbitol | − |
| | | mannitol, xylose | |
| | | melibiose, cellobiose | − |
| | | myo-inositol | |
| plant hormones | 6.5 $\mu$g · ml$^{-1}$ | kinetine | − |

TABLE 2-continued

Influence of a number of low-molecular substances on the induction of the virC-promotor

| Tested substances | Induction virC in E. coli del. lac. (pMP31) |
|---|---|
| naphthalene acetic acid | − |

TABLE 3

Treatment of exudates with enzymes and the influence hereof on the induction of the virC-promotor

| Treatment of exudates with | Induction virC pro motor | Induction of lacZ in control Flac+:del (lac-pr |
|---|---|---|
| RNase | + | + |
| DNase | + | + |
| phospholipase A2 | + | + |
| phospholipase D | + | + |
| pronase (20 μg · ml$^{-1}$) | − | − |
| trypsine (20 μg · ml$^{-1}$) | − | + |

We claim:

1. A process for activating genes in microorganisms comprising incubating a microorganism containing a gene-promoter construct with a plant, or plant exudate or a portion thereof, said gene-promoter construct having a promoter controlling the expression of a gene to be activated, said promoter in the gene promoter construct comprising the vir promoter, said gene to be activated being one not naturally present with the promoter in said construct.

2. The process, as in claim 1, wherein the promoter in the gene promoter construct comprises the virC promoter.

3. The process, as in claim 2, wherein the gene is a naturally occurring gene.

4. The process, as in claim 2 wherein the plant or exudate is from dicotyledonous plant.

5. The process, as in claim 1, wherein the microorganism is a bacterium.

6. The process as in claim 5 wherein the bacterium is E. coli.

7. The process, as in claim 6 wherein the gene in the gene-promoter construct to be activated is contained on plasmid pMP 31.

8. The process, as in claim 6 wherein no transfer of the gene promoter construct to the plant cells occurs.

9. The process, as in claim 5, wherein the bacterium is Agrobacterium tumefaciens.

10. The process, as in claim 5 wherein the gene in the gene-promoter construct to be activated is contained in a cointegrate plasmid formed as a cointegrate of pMP31 and a second plasmid having a host range which includes Agrobacterium, whereby the cointegrate plasmid may be stably introduced into Agrobacterium for activation of the gene.

11. The process, as in claim 1 wherein the activator substance comprises newly germinated seeds or root tissue.

12. The process, as in claim 1 wherein the plant exudates are onion exudates.

13. A process for producing substances that are detrimental to microorganisms comprising incubating microorganisms containing a vir C promoter construct with an activator substance consisting of a plant exudate, plant or portion thereof in a culture medium, said promoter construct having a gene coding for a substance detrimental to said microorganisms, and isolating the substance which is detrimental to the microorganisms from the medium.

14. A process for the treating of crops comprising incubating a microorganism containing a vir C promoter construct with plant crops, said construct comprising a gene to be activated and a vir C promoter, said promoter controlling the expression of said gene, said gene being one that is not naturally present with said promoter in said construct.

15. The process, as in claim 14 wherein the gene codes for a siderophore.

16. The process, as in claim 14, wherein the microorganism is a Pseudomonas.

17. A process for producing substances that are growth inhibiting to microorganisms comprising incubating microorganisms containing a virC promoter construct with an activator substance consisting of a plant, plant exudate or portion thereof in a culture medium, the promoter construct coding for a substance inhibiting to said microorganism and isolating the substance which is inhibiting to the microorganism from the medium.

* * * * *